US009517091B2

United States Patent
Lange et al.

(10) Patent No.: US 9,517,091 B2
(45) Date of Patent: Dec. 13, 2016

(54) LOCKING MECHANISM

(71) Applicant: Warsaw Orthopedic, Inc., Warsaw, IN (US)

(72) Inventors: Eric C. Lange, Collierville, TN (US); Darren L. Davis, Arlington, TN (US)

(73) Assignee: Warsaw Orthopediac, Inc., Warsaw, IN (US)

( * ) Notice: Subject to any disclaimer, the term of this patent is extended or adjusted under 35 U.S.C. 154(b) by 368 days.

(21) Appl. No.: 13/840,405

(22) Filed: Mar. 15, 2013

(65) Prior Publication Data

US 2014/0277138 A1 Sep. 18, 2014

(51) Int. Cl.
A61B 17/70 (2006.01)
A61B 17/80 (2006.01)

(52) U.S. Cl.
CPC ....... *A61B 17/7059* (2013.01); *A61B 17/7068* (2013.01); *A61B 17/8047* (2013.01)

(58) Field of Classification Search
CPC ............ A61B 17/7062; A61B 17/7067; A61B 17/7068; A61B 17/7059; A61B 17/8047; A61B 2017/347
USPC ................................ 606/246–260; 623/17.11
See application file for complete search history.

(56) References Cited

U.S. PATENT DOCUMENTS

| | | | |
|---|---|---|---|
| 5,279,575 A * | 1/1994 | Sugarbaker | A61B 17/3403 604/104 |
| 5,810,712 A * | 9/1998 | Dunn | A61B 90/50 600/114 |
| 7,455,328 B2 | 11/2008 | Chelchowski et al. | |
| 8,308,768 B2 | 11/2012 | Fauth | |
| 8,343,190 B1 * | 1/2013 | Mueller et al. | 606/248 |
| 9,072,550 B2 * | 7/2015 | Lange | A61B 17/7067 |
| 2006/0247640 A1 * | 11/2006 | Blackwell et al. | 606/71 |
| 2007/0090238 A1 * | 4/2007 | Justis | 248/181.1 |
| 2008/0167688 A1 | 7/2008 | Fauth et al. | |
| 2010/0087869 A1 * | 4/2010 | Abdou | 606/279 |
| 2010/0148455 A1 | 6/2010 | Taguchi | |
| 2010/0268279 A1 * | 10/2010 | Gabelberger et al. | 606/278 |
| 2011/0004251 A1 * | 1/2011 | Sweeney et al. | 606/264 |
| 2011/0319936 A1 * | 12/2011 | Gordon et al. | 606/248 |
| 2014/0277138 A1 * | 9/2014 | Lange | A61B 17/7059 606/246 |
| 2014/0277171 A1 * | 9/2014 | Lange | A61B 17/7067 606/279 |
| 2015/0173806 A1 * | 6/2015 | Lange | A61B 17/7068 606/248 |

* cited by examiner

*Primary Examiner* — Jacqueline Johanas

(57) ABSTRACT

A spinal implant includes a locking mechanism. The locking mechanism includes an inner surface defining a tapered passageway. A tapered collet is configured for disposal in the tapered passageway. The tapered collet has an inner surface defining a passageway configured for disposal of a longitudinal member. The tapered collet is configured to translate within the tapered passageway between a non-locking orientation in which the longitudinal member is moveable relative to the tapered collet and a locking orientation in which the longitudinal member is fixed relative to the tapered collet.

12 Claims, 5 Drawing Sheets

LOCKING MECHANISM

TECHNICAL FIELD

The present disclosure generally relates to medical devices for the treatment of musculoskeletal disorders, and more particularly to a locking mechanism used during treatment of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as fixation devices, for stabilization of a treated section of a spine. This disclosure describes an improvement over these prior art technologies.

SUMMARY

Accordingly, a spinal implant is provided. In one embodiment, in accordance with the principles of the present disclosure, the spinal implant includes a locking mechanism. The locking mechanism includes an inner surface defining a tapered passageway. A tapered collet is configured for disposal in the tapered passageway. The tapered collet has an inner surface defining a passageway configured for disposal of a longitudinal member. The tapered collet is configured to axially translate within the tapered passageway between a non-locking orientation such that the longitudinal member is axially moveable within the passageway of the tapered collet and a locking orientation such that the longitudinal member is fixed relative to the tapered collet.

In one embodiment, in accordance with the principles of the present disclosure, the locking mechanism includes an outer member including an inner surface defining a first passageway. The first passageway defines a first central axis along its length. An inner member is engaged to the inner surface of the outer member and defines a second central axis along its length. The inner member includes an inner surface defining a second passageway configured for disposal of a longitudinal member. The second passageway defines a third central axis along its length offset from the second central axis. The locking mechanism is configured to rotate between a non-locking orientation in which the first and third central axes are co-axial such that the longitudinal member is movable relative to the inner and outer members and a locking orientation in which the first and third central axes are offset such that the longitudinal member is fixed relative to the inner and outer members.

In one embodiment, in accordance with the principles of the present disclosure, the locking mechanism includes a wall having an inner surface defining an arcuately shaped first passageway. An outer member is disposable with the inner surface of the wall. The outer member includes an inner surface defining an arcuately shaped second passageway having a first central axis along its length. An inner member extends between a proximal end and a distal end disposable within the second passageway. The inner member defines a second central axis along its length. The inner member includes an inner surface defining a third passageway extending between the proximal and distal ends configured for disposal of a longitudinal member. The third passageway defines a third central axis along its length offset from the second central axis. The locking mechanism is configured to rotate between a non-locking orientation in which the first and third central axes are co-axial and the longitudinal member is movable relative to the inner and outer members and a locking orientation in which the first axis is offset from the third axis and the longitudinal member is fixed relative to the inner and outer members.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
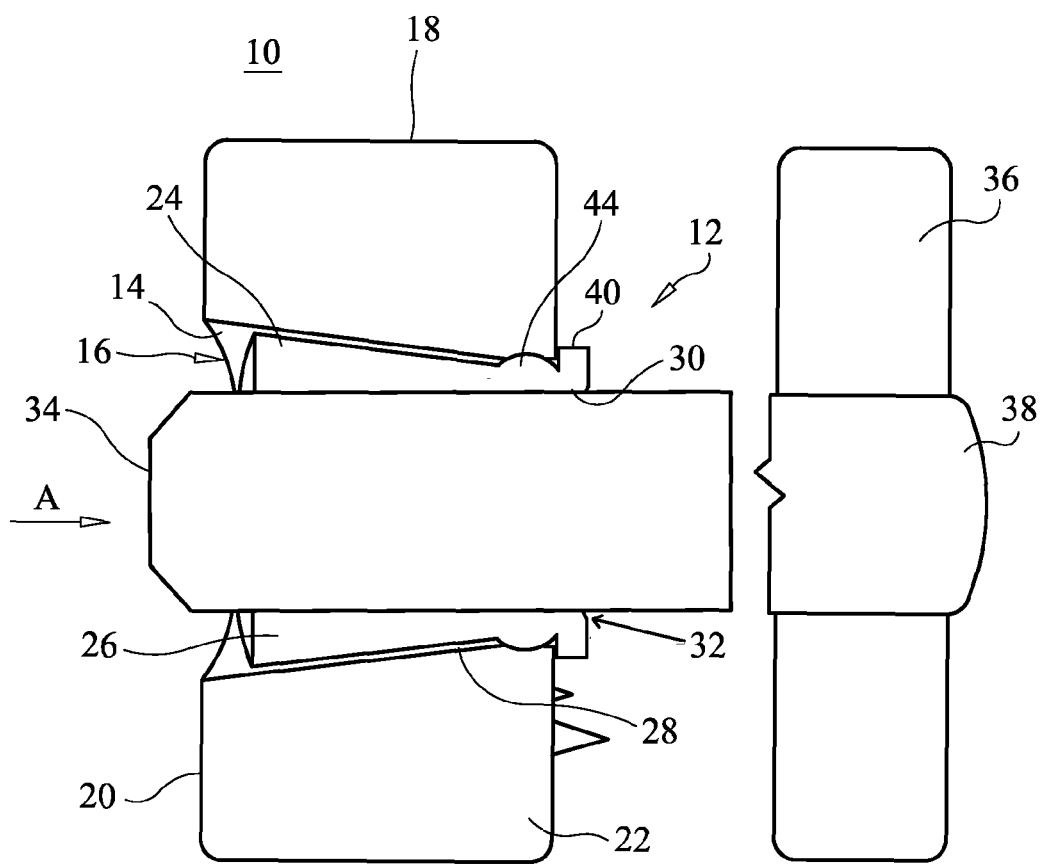
FIG. 1 is a side, cross sectional view of one embodiment of a spinal implant according to the principles of the present disclosure.

The exemplary embodiments of the surgical system and related methods of use disclosed are discussed in terms of medical devices for the treatment of musculoskeletal disorders and more particularly, in terms of a spinal implant including a locking mechanism for locking a spinal implant. It is envisioned that the spinal implant may be employed in applications such as correction of deformities such as kyphosis, scoliosis. For example, the spinal implant can include an interspinous process plate fixation device incorporating a locking mechanism.

In one embodiment, a locking mechanism is provided for locking a longitudinal member, such as, for example, a spinal rod, post or screw relative to a surface, such as, for example, a spinal plate. The locking mechanism includes a tapered lock that creates an interference fit between an inside taper of a plate and a tapered collet. The tapered collet possesses a snap feature that will resist engagement of the locking taper and allow translation of the plate until a force is applied to the tapered collet to release the snap. The applied force to engage the tapered collet with the inside taper of the plate can occur by an instrument or the plate and collet can possess threads where a nut can create the applied force for locking the locking mechanism.

In one embodiment, a locking mechanism includes a tapered lock with a spherical collar that can be pressed into position so as to create an interference fit between an inside taper of the spherical collar and a tapered collet. The tapered collet possesses a snap feature that will resist engagement of the locking taper and allow translation of a plate until a force is applied to the tapered collet to release the snap. The applied force to engage the tapered collet with the inside taper of the spherical collar can occur by an instrument or the spherical collar and collet can possess threads where a nut can create the applied force to lock the locking mechanism. This locking feature can restrict translation and orbital motion of the plate. In one embodiment, the spherical collar is slit such that the spherical feature will expand and cause an interference fit between the outside of the sphere and the inside of the plate as the tapered collet is pressed into the inside of the sphere's inside taper. In one embodiment, the spherical collar does not have a slit to retain orbital motion after translational motion is restricted.

In one embodiment, a locking mechanism includes an off center axis locking nut that can be threaded to a position which will align inside hole features between an inside cylinder and an outside cylinder. Twisting of the outside cylinder will rotate the axis of the outside cylinder to create an interference fit between both cylinders and a post or screw. The outside cylinder may or may not possess a break off feature to control applied torque to lock the locking mechanism onto the post. An outside cylinder removal nut can be used for disengagement of the locking nut. This locking feature can restrict translation of a plate along the post or screw. A spherical tip on the outer cylinder can allow the plate to orbit about a fixed point on the axis of the post. In one embodiment, the inside cylinder is affixed to the plate and the outside cylinder is threaded away from the plate to lock the locking mechanism. This would restrict both orbital motion and translational motion.

In one embodiment, a locking mechanism includes a two piece off center axis locking nut with an outer sphere that can be twisted to a position which will align two inside hole features of the two components to allow insertion and smooth translation of a post or screw. Twisting of a proximal hex nut feature of the outside cylinder will rotate the two axes out of alignment to create an interference fit between the two piece locking nut which will expand the locking nut and grip the inside of a plate and the post or screw. The locking nut may or may not possess a break off feature to control applied torque to lock the locking mechanism onto the post. A proximal hex nut can be used for disengagement of the locking nut. This locking feature can restrict translation of the plate along the post. The outer spherical feature can be slit to allow expansion and interference within the plate to lock both orbital and translational motion. In one embodiment, the outer sphere does not have a slit, which will result in a restriction only of translational motion. A connection between the plate and post can be assembled with different length posts at the surgery to accommodate patient anatomy. In one embodiment, the post or screw can be removable from the plate by compressing a snap ring, removal of a set screw or pin, or loosening of a clamp.

It is contemplated that one or all of the components of the spinal implant may be disposable, peel-pack, pre-packed sterile devices. One or all of the components of the spinal implant may be reusable. The spinal implant may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of a spinal implant 10 can be fabricated from biologically acceptable materials suitable for medical applications, including metals, synthetic polymers, ceramics and bone material and/or their composites, depending on the particular application and/or preference of a medical practitioner. For example, the components of spinal implant 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of correction system 10 may have material composites, including the above materials, to achieve various desired characteristics such as strength, rigidity, elasticity, compliance, biomechanical performance, durability and radiolucency or imaging preference. The components of spinal implant 10, individually or collectively, may also be fabricated from a heterogeneous material such as a combination of two or more of the above-described materials. The components of spinal implant 10 may be monolithically formed, integrally connected or include fastening elements and/or instruments, as described herein.

Spinal implant 10 is employed, for example, with an open, mini-open or minimally invasive surgical technique to provide stabilization of a spine or other musculoskeletal structure. In preferred embodiments, the spinal implant 10 is configured to be integrated with instrumentation to allow for one hand insertion and implantation to stabilize two adjacent vertebrae for any surgical procedure requiring the same.

Turning now to FIGS. 1-8, there is illustrated components of a spinal implant 10 that includes a locking mechanism 12 in accordance with the principles of the present disclosure.

Referring to FIG. 1, locking mechanism 12 includes an inner surface 14 defining a tapered passageway 16. Inner surface 14 is arcuately shaped and has a low surface roughness Ra. It is contemplated that inner surface 14 has various surface configurations, such as, for example, rough, threaded, arcuate, undulating, porous, semi-porous, dimpled, polished and/or textured. It is further contemplated that inner surface 14 is variously shaped, such as, for example, oval, oblong, triangular, square, hexagonal, polygonal, irregular, uniform and/or non-uniform. Inner surface 14 can be defined by a wall, such as, for example, a spinal plate 18. Spinal plate 18 includes a first surface 20 and a second surface 22 configured to engage tissue, such as, for example, bone. Tapered passageway 16 extends between first and second surfaces 20, 22 of plate 18. Tapered passageway 16 has an arcuate cross section that uniformly decreases in diameter from first surface 20 to second surface 22.

Locking mechanism 12 includes a tapered collet 24 configured to transition between a locking orientation and a non-locking orientation. In the locking orientation, collet 24 restricts the axial translation and/or axial rotation of a longitudinal member. In the non-locking orientation, collet 24 does not restrict the axial translation and/or axial rotation of longitudinal member 34. Collet 24 is configured for disposal in tapered passageway 16. Tapered collet 24 extends between a proximal end 26 and a distal end 28. Tapered collet 24 has a conical configuration. In one embodiment, tapered collet 24 is a wedge. Collet 24 has an arcuate cross section configuration having a uniformly decreasing diameter from proximal to distal ends 26, 28 corresponding to tapered passageway 16. As collet 24 is inserted within passageway 16 in direction A as shown in FIG. 1, an interference fit between collet 24 and inner surface 14 forms such that collet 24 resists further axially translation through passageway 16. Collet 24 includes an inner surface 30 defining a passageway 32 configured for disposal of a longitudinal member 34, such as for example, a post, rod, or a screw, such as, for example, a bone screw. Passageway 32 has a uniform cross section along its length. Passageway 32 can have various cross section configurations, such as, for example, oval, oblong, triangular, square, hexagonal, and/or polygonal to accommodate variously shaped longitudinal members. In one embodiment, longitudinal member 34 is keyed to inner surface 30 of collet 24 such that longitudinal member 34 is restricted from rotating within passageway 32. In one embodiment, spinal implant 10 includes a second spinal plate 36 disposed about a distal end 38 of longitudinal member 34.

Collet 24 includes an abutting edge 40 disposed at distal end 28 configured to engage second surface 22 of wall or plate 18 in the non-locking orientation. Abutting edge 40 extends substantially perpendicular from an outer surface of collet 24. Abutting edge 40 resists axial translation of collet 24 in a distal-proximate direction. In one embodiment, inner surface 14 of wall 18 includes an arcuate notch or groove 42 adjacent second surface 22. Collet 24 includes an arcuate projection 44 disposed proximally adjacent to abutting edge 40. Arcuate projection 44 is configured for disposal in arcuate groove 42 in the non-locking orientation. In the locking orientation, arcuate projection 44 abuts second surface 22 so as to resist axial translation of collet 24 in the distal-proximate direction. In one embodiment, collet 24 does not include arcuate projection 44 and inner surface 14 does not include groove 42.

Figure 2:
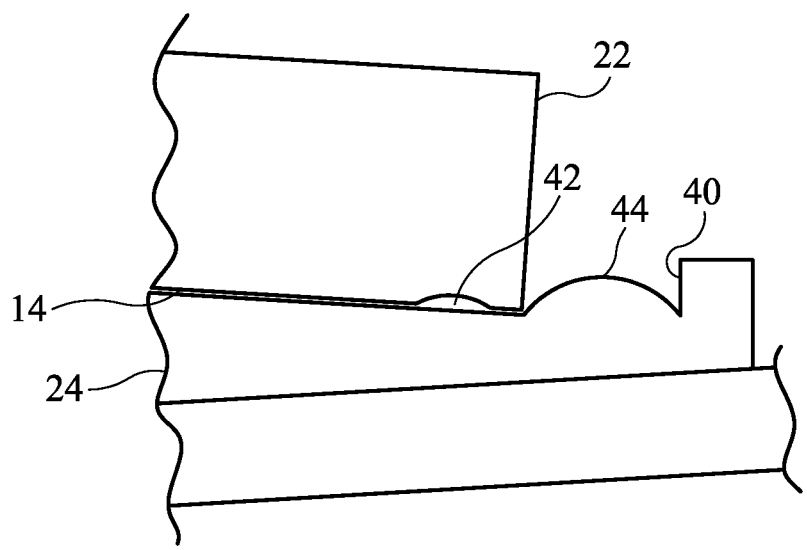
FIG. 2 is an expanded, side view of components of the implant shown in FIG. 1 in a locking orientation.
Figure 3:
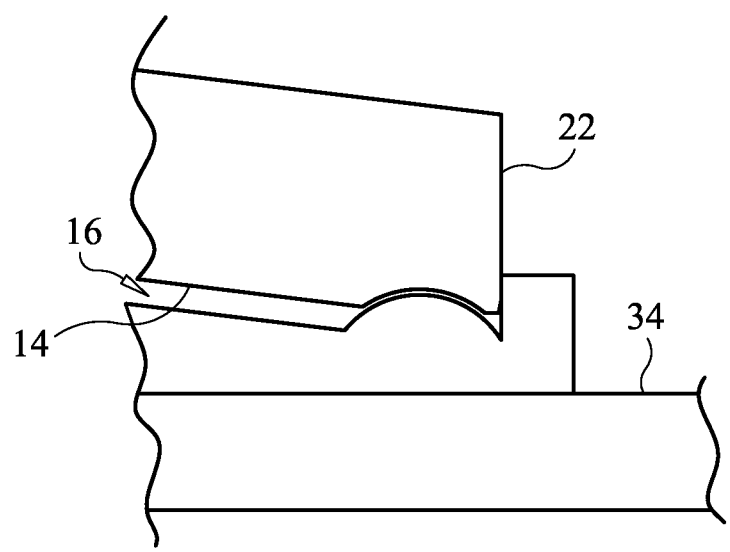
FIG. 3 is an expanded, side view of components of the implant shown in FIG. 1 in a non-locking orientation.

In operation, tapered collet 24 axially translates within tapered passageway 16 between the non-locking orientation and the locking orientation. In the non-locking orientation, as shown in FIG. 3, abutting edge 40 is in contact with second surface 22 and arcuate projection 44 is disposed in groove 42. As collet 24 is axially translated in a proximal-distal direction, such as, for example, the direction shown by arrow A, collet 24 becomes increasingly resistive to further movement and the frictional engagement between collet 24 and inner surface 14 increases causing passageway 32 of collet 24 to constrict about longitudinal member 34 orienting collet 24 in the locking orientation, as shown in FIG. 2. In the locking orientation, collet 24 resists the axial translation of longitudinal member 34 within passageway 32. In the locking orientation, arcuate projection 44 is disposed outside of passageway 16 and abuts second surface 22 resisting the movement of collet 24 in the distal-proximate direction.

Figure 4:
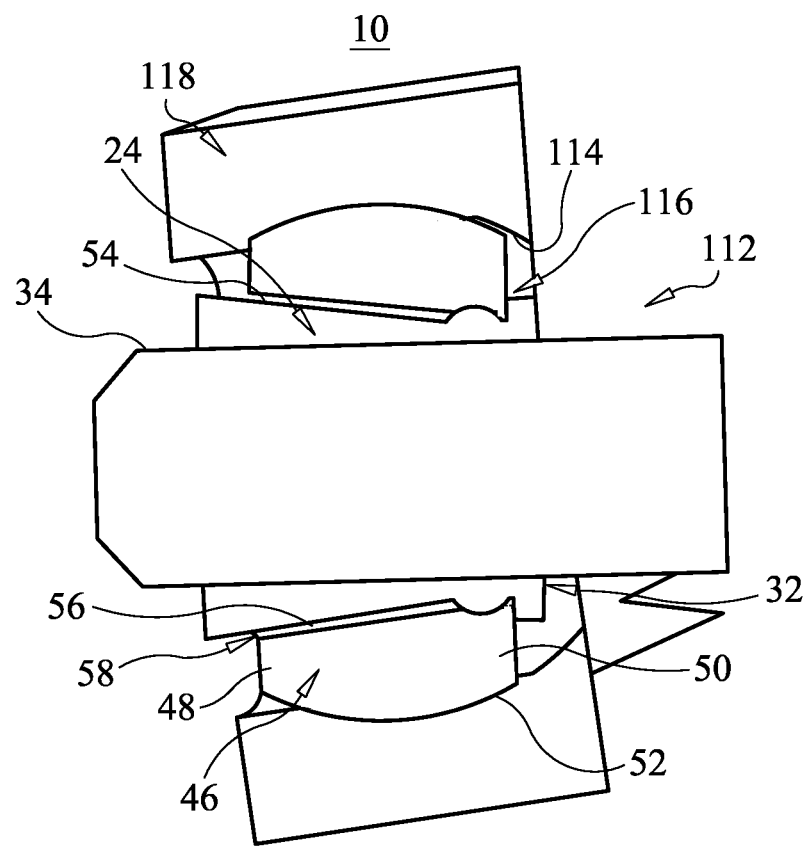
FIG. 4 is a perspective, cross sectional view of one embodiment of a spinal implant according to the principles of the present disclosure.
Figure 5:
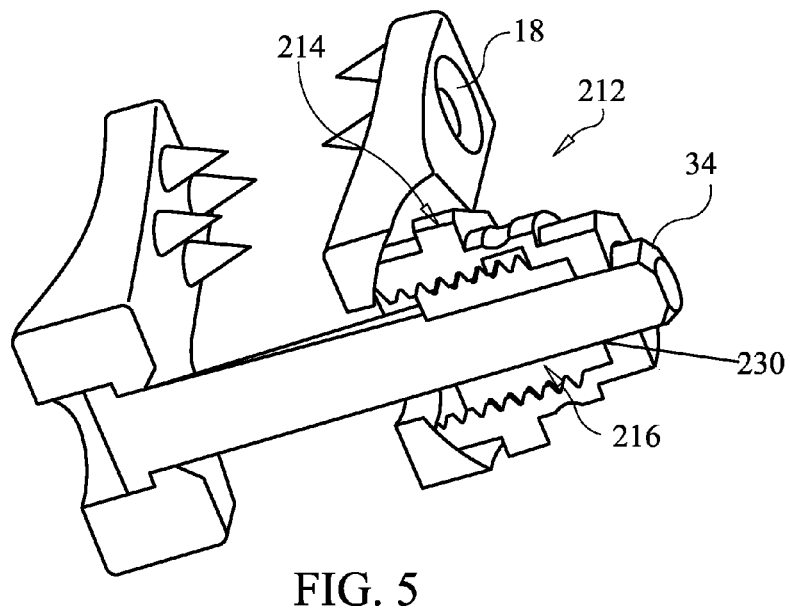
FIG. 5 is a perspective, cross-sectional view of one embodiment of a spinal implant according to the principles of the present disclosure.
Figure 6A:
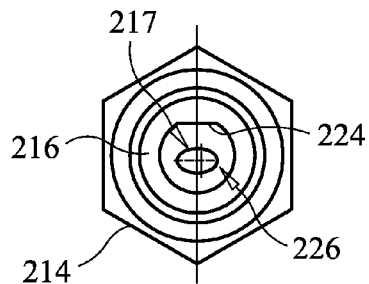
FIG. 6A is an end view of components of the implant shown in FIG. 5.
Figure 6B:
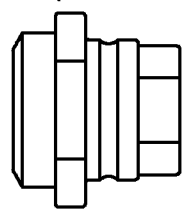
FIG. 6B is a side view of a component of the implant shown in FIG. 5.
Figure 6C:
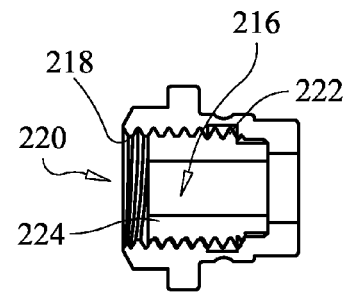
FIG. 6C is a side, cross-sectional view of components of the implant shown in FIG. 5.

In one embodiment, as shown in FIG. 4, spinal implant 10 includes a locking mechanism 112, similar to locking mechanism 12 described above. Locking mechanism 112 includes collet 24. Locking mechanism 112 further includes an arcuate collar 46 extending between a proximal end 48 and a distal end 50. Arcuate collar 46 has a spherical shape having a rounded outer surface 52. It is contemplated that arcuate collar 46 is variously shaped, such as, for example, those alternatives described herein. In one embodiment, arcuate collar 46 includes a slit 54 that extends between proximal and distal ends 48, 50 so that collar 46 can be dilated. Arcuate collar 46 includes an inner surface 56 defining a tapered passageway 58, similar to tapered passageway 16 described above. Tapered passageway 58 extends between proximal and distal ends 48, 50 of arcuate collar 46. Tapered passageway 58 is configured for disposal of collet 24.

Locking mechanism 112 further includes a wall, such as, for example, a spinal plate 118, similar to plate 18 described above. Plate or wall 118 has an inner surface 114 that defines a spherical passageway 116 configured for disposal of arcuate collar 46 such that arcuate collar 46 is rotatable within spherical passageway 116. It is contemplated that passageway 116 is variously shaped, such as, for example, those alternatives described herein.

In operation, as tapered collet 24 is axially translated within passageway 58 towards distal end 50 of arcuate collar 46 in a proximal-distal direction, arcuate collar 46 dilates or expands about tapered collet 24 to engage inner surface 114 of plate 118 orienting collet 24 in the locking orientation. In the locking orientation, longitudinal member 34 is prevented from axially translating and/or rotating relative to inner surface 114 of plate 118. In the locking orientation, as described above with regard to FIGS. 1-3, longitudinal member 34 is also prevented from axially translating within passageway 32 of tapered collet 24. In the embodiment in which arcuate collar 46 does not include slit 54, as tapered collet 24 is axially translated towards distal end 50 of arcuate collar 46 in the proximal-distal direction, arcuate collar 46 does not expand, which allows for the continued rotation of collar 46 relative to inner surface 114 of plate 118, but still resists axial translation of longitudinal member 34 within passageway 32 of collet 24.

In one embodiment, as shown in FIGS. 5 and 6A-6C, there is shown a locking mechanism 212. Locking mechanism 212 includes an outer member, such as, for example, a hex nut 214, and an inner member, such as, for example, a cylinder 216 disposable within hex nut 214 in a non-concentric configuration. Hex nut 214 includes an inner surface 218 defining a first passageway 220. Inner surface 218 is threaded. It is contemplated that inner surface 218 has various surface configurations, such as, for example, rough, arcuate, undulating, porous, semi-porous, dimpled, polished and/or textured. First passageway 220 defines a first central axis along its length.

Cylinder 216 includes a threaded outer surface 222 threadedly engaged to inner surface 218 of hex nut 214. It is contemplated that outer surface 222 has various surface configurations to enhance engagement with hex nut 214, such as, for example, those alternatives described herein. Cylinder 216 defines a second central axis along its length. Cylinder 216 includes an inner surface 224 defining a second passageway 226 configured for disposal of longitudinal member 34. Longitudinal member 34 is keyed to inner surface 224 such that when longitudinal member 34 is disposed in second passageway 226, longitudinal member 34 is prevented from rotating relative to inner surface 224 of cylinder 216. Second passageway 226 defines a third central axis along its length offset from the second central axis of cylinder 216, as shown by 217 in FIG. 6A. Cylinder 216 has a wall thickness that varies along its circumference creating the offset 217 between second and third central axes of cylinder 216 and second passageway 226, respectively. In one embodiment, the second central axis of cylinder 216 is offset from a central axis of hex nut 214.

In operation, locking mechanism 212 rotates between a non-locking orientation and a locking orientation. When locking mechanism 212 is in the non-locking orientation, the first and third central axes are co-axial so as to receive longitudinal member 34 and longitudinal member 34 is movable relative to hex nut 214 and cylinder 216. Once longitudinal member 34 is disposed within second passageway 226, hex nut 214 or cylinder 216 is rotated with respect to one another. Upon rotation of hex nut 214 with respect to cylinder 216, the first and third central axes become offset relative to one another, locking longitudinal member 34 relative to hex nut 214 and cylinder 216. When longitudinal member 34 is fixed relative to hex nut 214 and cylinder 216, locking mechanism 212 is in the locking orientation. When locking mechanism 212 is in the locking orientation, inner surfaces 218, 224 of hex nut 214 and cylinder 216, respectively, frictionally engage longitudinal member 34 in region 230.

Figure 7:
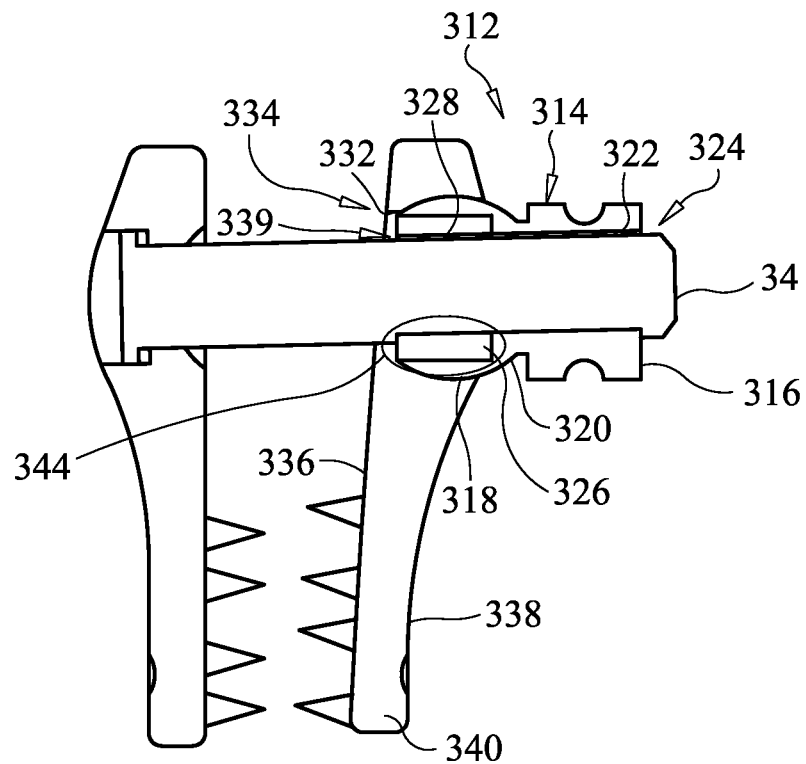
FIG. 7 is a side, cross-sectional view of one embodiment of a spinal implant according to the principles of the present disclosure.

In one embodiment, shown in FIG. 7, a locking mechanism 312 is provided, similar to locking mechanism 212 described above with regard to FIGS. 5 and 6A-6C. Locking mechanism 312 includes an outer member 314, similar to hex nut 214 described above. Outer member 314 extends between a cylindrically shaped proximal end 316 and a distal end 318. Distal end 318 includes an arcuate collar 320, similar to collar 24 described above with regard to FIG. 4. Outer member 314 includes an inner surface 322 that defines a first passageway 324 along its length. First passageway 324 defines a first central axis along its length.

Locking mechanism 312 includes an inner member, such as, for example, an inner cylinder 326 disposed with first passageway 324. Cylinder 326 defines a second central axis along its length. Cylinder 326 includes an inner surface 328 defining a second passageway 330 configured for disposal of longitudinal member 34. Longitudinal member 34 is keyed to inner surface 328 such that when longitudinal member 34 is disposed in second passageway 330, longitudinal member 34 is prevented from rotating relative to inner surface 328 of cylinder 326. Second passageway 330 defines a third central axis along its length offset from the second central axis of cylinder 326, similar to locking mechanism 212. Cylinder 326 has a wall thickness that varies along its circumference creating the offset between second and third central axis of cylinder 326 and second passageway 330, respectively. In one embodiment, outer member 314 has a varying wall thickness along its circumference so that second central axis of cylinder 326 is offset from a central axis of outer member 314.

Locking mechanism 312 further includes an inner surface 332 defining an arcuately shaped third passageway 334. Third passageway 334 extends between surfaces 336, 338 of a wall or plate 340, similar to plate 18 described above. Arcuate collar 320 of outer member 314 is disposed with third passageway 334 between inner surface 332 of wall or plate 340 and an outer surface of cylinder 326. With arcuate collar 320 disposed in third passageway 334, outer member 314 is rotatable about an axis transverse to the first central axis.

In operation, locking mechanism 312 rotates between a non-locking orientation and a locking orientation. When locking mechanism 312 is in the non-locking orientation, the first and third central axes are in substantially co-axial alignment so as to receive longitudinal member 34. Once longitudinal member 34 is disposed within second passageway 330, outer member 314 and cylinder 326 are rotated with respect to one another. Upon rotation of outer member 314 with respect to cylinder 326, for example, the first and third central axes become increasingly offset causing outer member 314 to dilate or expand such that collar 320 forcefully engages inner surface 332 of wall 340. When locking mechanism 312 is in the locking orientation, the first and third central axes are offset such that inner surfaces 328, 322 of cylinder 326 and outer member 314, respectively, frictionally engage longitudinal member 34 in region 344 preventing axial and/or rotational movement of longitudinal member 34. In one embodiment, outer member 314 does not dilate or expand as outer member 314 is rotated with respect to cylinder 326 such that longitudinal member 34 is rotatable.

Figure 8:
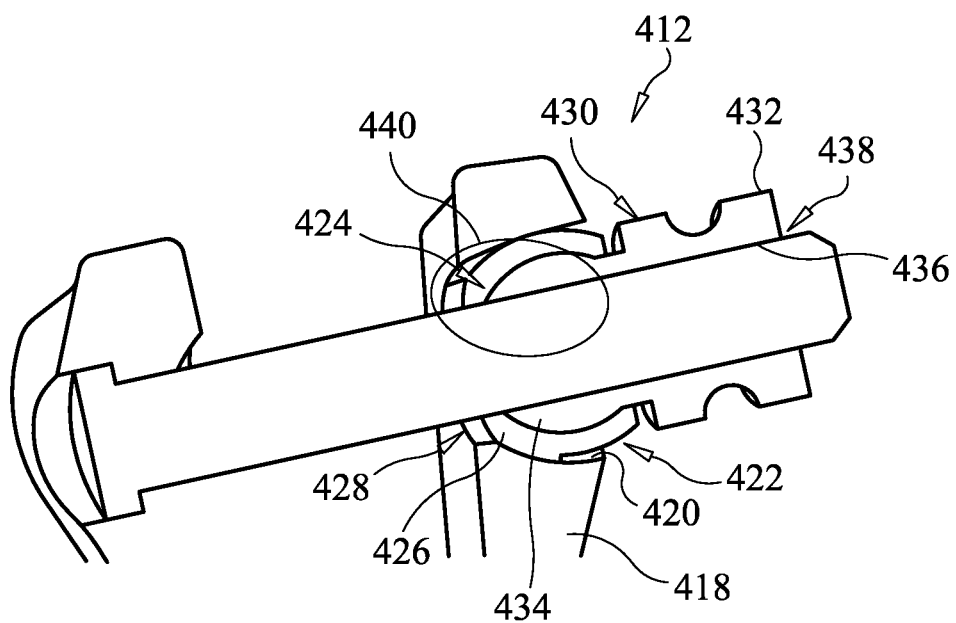
FIG. 8 is a side, cross sectional view of one embodiment of a spinal implant according to the principles of the present disclosure.

In one embodiment, shown in FIG. 8, a locking mechanism 412 is provided, similar to locking mechanism 312 described above. Locking mechanism 412 includes a wall, such as, for example, a spinal plate 418. Plate 418 includes an inner surface 420 defining an arcuately shaped first passageway 422.

Locking mechanism 412 includes an outer member, such as, for example, an outer collar 424, similar to collar 24 described above with regard to FIG. 4. Collar 424 is disposable with passageway 422 of plate 218. Collar 424 includes an inner surface 426 defining an arcuately shaped second passageway 428 having a first central axis along its length.

Locking mechanism 412 includes an inner member 430, similar to outer member 314 described above, extending between a proximal end 432 and a distal end 434. Proximal end 432 includes a hex nut and distal end 434 includes an inner arcuate collar 434. Inner arcuate collar 434 is disposable with second passageway 428. Inner member 430 includes an inner surface 436 defining a third passageway 438 extending between proximal and distal ends 432, 434. Third passageway 438 is configured for disposal of longitudinal member 34. Third passageway 438 defines a third central axis along its length offset from the second central axis.

In operation, locking mechanism 412 rotates between a non-locking orientation and a locking orientation. When locking mechanism 412 is in the non-locking orientation, the first and third central axes are co-axial so as to receive longitudinal member 34 such that longitudinal member is movable relative to inner member 430 and collar 424. Once longitudinal member 34 is disposed within third passageway 438, outer collar 424 and inner member 430 are rotated with respect to one another. Upon rotation of collar 424 with respect to inner member 430, for example, the first and third central axes become offset causing outer collar 424 to dilate or expand such that collar 424 forcefully engages inner surface 420 of wall 418. When locking mechanism 412 is in the locking orientation, with first and third central axes being offset, inner surfaces 436, 426 of inner member 430 and collar 424, respectively, frictionally engage longitudinal member 34 in region 440 preventing axial and rotational movement of longitudinal member 34. In one embodiment, outer collar 424 does not dilate or expand as collar 424 rotates with respect to inner member 430 such that longitudinal member 34 remains rotatable.

In one embodiment, spinal implant 10 may be treated with or include an agent, which may be disposed, packed or layered within, on or about the components and/or surfaces of spinal implant 10. It is envisioned that the agent may include bone growth promoting material, such as, for example, bone graft to enhance spinal implant 10 with spinal processes of vertebrae.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of fixation system 10 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant including a locking mechanism, the locking mechanism comprising:
   a spinal plate;

an arcuate collar rotatably disposed in the spinal plate, the arcuate collar comprising an inner surface defining a tapered passageway;
a longitudinal member; and
a tapered collet configured for disposal in the tapered passageway, the tapered collet having an inner surface defining a passageway configured for disposal of the longitudinal member,
wherein the tapered collet is configured to translate between a non-locking orientation in which the longitudinal member is moveable within the passageway of the tapered collet and a locking orientation in which the longitudinal member is fixed relative to the arcuate collar and the tapered collet to prevent translation of the longitudinal member while allowing rotation of the arcuate collar and the longitudinal member relative to the spinal plate.

2. A spinal implant as recited in claim 1, wherein the spinal plate includes a first surface and a second surface configured to engage tissue, the plate defining a spherical passageway having the arcuate collar rotatably disposed therein, the spherical passageway extending between the first and second surfaces.

3. A spinal implant as recited in claim 2, wherein the tapered collet extends between a proximal end and a distal end, the distal end including an abutting edge configured to engage a side surface of the arcuate collar that extends transverse to the first and second surfaces when the tapered collet is in the non-locking orientation.

4. A spinal implant as recited in claim 3, wherein the passageway of the arcuate collar is tapered and includes an arcuate groove, the tapered collet including an arcuate projection disposed adjacent to the abutting edge, the arcuate projection being configured for disposal in the arcuate groove when the tapered collet is in the non-locking orientation.

5. A spinal implant as recited in claim 1, wherein the tapered collet has a conical configuration.

6. A spinal implant as recited in claim 1, wherein the tapered collet includes a wedge.

7. A spinal implant as recited in claim 2, wherein the spinal implant includes a second spinal plate disposed about a distal end of the longitudinal member.

8. A spinal implant as recited in claim 1, wherein the arcuate collar extends between a proximal end and a distal end, the passageway of the arcuate collar being tapered from the proximal end of the arcuate collar to the distal end of the arcuate collar.

9. A spinal implant as recited in claim 1, wherein the spinal plate includes an inner surface defining a spherical passageway configured for disposal of the arcuate collar such that the arcuate collar is rotatable within the spherical passageway.

10. A spinal implant as recited in claim 9, wherein the tapered collet has a conical configuration.

11. A spinal implant as recited in claim 9, wherein the arcuate collar includes a slit extending between proximal and distal ends of the arcuate collar, and wherein when the tapered collet is axially translated towards the distal end of the arcuate collar, the arcuate collar being configured to expand about the tapered collet to engage the inner surface of the spinal plate so as to move the tapered collet into the locking orientation.

12. A spinal implant as recited in claim 1, wherein the longitudinal member is a post or a bone screw.

\* \* \* \* \*